United States Patent
Vortman et al.

(10) Patent No.: US 6,705,994 B2
(45) Date of Patent: Mar. 16, 2004

(54) TISSUE INHOMOGENEITY CORRECTION IN ULTRASOUND IMAGING

(75) Inventors: Kobi Vortman, Haifa (IL); Shuki Vitek, Haifa (IL)

(73) Assignee: Insightec - Image Guided Treatment LTD (IL)

( * ) Notice: Subject to any disclaimer, the term of this patent is extended or adjusted under 35 U.S.C. 154(b) by 0 days.

(21) Appl. No.: 10/190,787

(22) Filed: Jul. 8, 2002

(65) Prior Publication Data

US 2004/0006272 A1 Jan. 8, 2004

(51) Int. Cl.[7] .................................................. A61B 8/00
(52) U.S. Cl. ...................................................... 600/443
(58) Field of Search .............................. 600/407–471; 367/7, 11, 130, 138, 155; 73/620–633; 128/916; 601/2, 3

(56) References Cited

U.S. PATENT DOCUMENTS

| | | | | |
|---|---|---|---|---|
| 4,915,115 A | * | 4/1990 | Sasaki et al. ................ | 600/441 |
| 5,515,342 A | * | 5/1996 | Stearns et al. ............... | 367/155 |
| 5,971,925 A | * | 10/1999 | Hossack et al. ............ | 600/443 |
| 5,984,881 A | * | 11/1999 | Ishibashi et al. ................ | 601/2 |

* cited by examiner

Primary Examiner—Ali M. Imam
(74) Attorney, Agent, or Firm—Bingham McCutchen LLP

(57) ABSTRACT

A method of imaging a site of interest in a body using an ultrasound probe comprising a plurality of ultrasound transducer elements comprises obtaining an ultrasound image of a pass zone between the ultrasound probe and the site of interest. The image includes the site of interest and a plurality of tissue regions in a pass zone between the site of interest and the ultrasound probe. Boundaries of a selected tissue region in the pass zone are determined from the image. Focusing delay times are then computed for each ultrasound transducer element based in part on the speed of sound in the selected tissue region other than an average speed of sound in body tissue, and the boundaries of the selected tissue region. Preferably, a speed about the speed of sound in the selected tissue region is used and more preferably the speed of sound in the selected tissue region is used. Refraction may be considered, as well. Ultrasound imaging of the site of interest is then conducted employing the computed delay times. Fat and bone tissue regions are typically selected if present. Other tissue regions may be selected, as well. The boundaries of the tissue region or regions may be determined by segmentation. Tissue inhomogeneity is thereby compensated for, improving image contrast resolution. Ultrasound imaging systems and software are also disclosed. A new ultrasound probe comprising high and low frequency transducer elements is also disclosed.

57 Claims, 10 Drawing Sheets

TISSUE INHOMOGENEITY CORRECTION IN ULTRASOUND IMAGING

FIELD OF THE INVENTION

The invention relates to ultrasound imaging and, more particularly, to correcting for variations in the speed of sound in different tissue types traversed by ultrasound beams during imaging.

BACKGROUND OF THE INVENTION

Ultrasound imaging systems produce images by detecting and analyzing echoes of high frequency ultrasound beams propagating through and reflected from body tissue. The ultrasound beams are typically transmitted by and then detected by an ultrasound probe, which may comprise a plurality of transducer elements in a transducer array. Each transducer element is driven by electrical signals to cause transmission of an ultrasound beam. To focus the ultrasound beams transmitted by each transducer element onto a focal point proximate a site of interest, transmission time delays ("transmission delays") are introduced to the signals driving each transducer element by a beam former so that the transmitted ultrasound beams constructively interfere at the focal point. The location of the focal point is typically selected by an operator of the ultrasound system. Sound waves reflected from the tissue at the site of interest and from tissue and other reflecting bodies between the focal point and the ultrasound probe (referred to as the pass zone) are also detected by the transducer elements in the array. Reflected sound waves are referred to as echo signals. The phases of the detected echo signals are also aligned by the introduction of reception time delays ("reception delays") to the detected signals prior to summing the signals. Images are reconstructed from the summed signals. Static and dynamic ultrasound images may be generated for analyzing the function of an organ and tissue morphology.

Image quality depends on many system-related factors, such as probe acoustical design, front end hardware and imaging frequency, as well as patient-related factors, such as tissue inhomogeneity and target reluctance, for example. Ultrasound imaging is difficult or impossible to perform on about 30% of patients due to patient-related factors.

Tissue inhomogeneity affects image quality because of the differing speed of sound through different types of tissue. The transmission delays for each signal driving each transducer element, as well as the reception delays for bringing echo signals into phase, are computed based on the distance from each transducer element to the focal point or reflecting body in the pass zone and an average speed of sound in body tissue. Sound travels through body tissue at an average speed of sound of 1540 m/s. Zagzebski, James A., Essentials of Ultrasound Physics, Mosby-Year Book, Inc., Missouri, (1996), p. 6. The average speed of sound in body tissue may vary for different individuals and other uniform speeds may be used as the average speed of sound. The range of values for the average speed of sound in body tissue is 1540 m/s plus or minus 3%. Furthermore, sound travels through different types of body tissue at different speeds. For example, the speed of sound through fat is 1460 m/s. The speed of sound through muscle is 1600 m/s. The speed of sound through bone tissue is much faster (3000 m/s for skull bone tissue, for example). The speed of sound will also vary in different organs. For example, the speed of sound in liver tissue is 1555 m/s. In kidney tissue, the speed of sound is 1565 m/s. (We note that there is some variability in the reported speeds of sound in different body tissues and the average speed of sound in body tissue due to variability among individuals).

During transmission of the ultrasound beams, these speed differences may shift the phase of the transmitted ultrasound beams, decreasing the constructive interference at the focal point. Image contrast resolution is thereby decreased. Such phase shifts also increase side lobes of the beam, further decreasing the image quality.

During detection and processing of echo signals, the arrival times of the echo signals are also shifted, decreasing contrast resolution and introducing geometrical errors into the image. For example, with an imaging depth of 10 cm, traversal of 3 cm of fat at a speed of 1460 m/s (instead of the average speed of 1540 m/s), will delay the arrival time of echo signals from the site of interest by about 1.3 microseconds. This can cause an error in location of a site of interest of about 2.5 mm in an image. Such an error could be detrimental in ultrasound guided medical procedures, such as needle biopsies, for example.

Tissue inhomogeneity also causes refraction of the ultrasound beams at the boundaries of tissue regions having different speeds of sound. Refraction may also decrease constructive interference at the focal point. While generally of lesser concern than phase shift in soft tissue, refraction caused by boundaries between bone and soft tissue can also seriously degrade contrast resolution of an ultrasound image.

Efforts to correct for patient-related factors have included analyzing the reflected signal and optimizing the detected echo signals and the reconstructed image based on predefined control parameters, in a manner similar to autofocusing. In U.S. Pat. No. 4,817,614, for example cross-correlation of ultrasound echo signals received at adjacent transducer elements of an ultrasound probe are used to identify and compensate for tissue inhomogeneities. First, a sectional plane of a subject is scanned. Then, unwanted effects caused by the inhomogeneities are measured for each transducer element, based on cross-correlation of the echo signals received by adjacent transducer elements in the probe. Correction values for the delay times are derived from the measured values and then the delay times are varied based on the correction values.

SUMMARY OF THE INVENTION

To correct for tissue inhomogeneity in accordance with the present invention, a speed of sound other than an average speed of sound in at least one selected tissue region in the pass zone is used in conjunction with the boundaries of the selected tissue region to determine focusing delay times (either transmission delays, reception delays or both). In particular, the actual speed of sound in the selected tissue region or a speed between the actual speed of sound and the average speed of sound, may be used. The closer the speed is to the actual speed of sound, the more accurate the correction. Sufficient correction will generally be provided by considering a speed of sound other than the average speed of sound for fat and bone tissue regions, if present. If further correction is desired or necessary, a speed of sound other than the average speed of sound in other tissue regions may be considered, as well.

In accordance with one embodiment of the invention, a method of imaging a site of interest in a body using an ultrasound probe, where the ultrasound probe comprises a plurality of ultrasound transducer elements, is disclosed. The method comprises obtaining an ultrasound image of a pass zone of the body between the site of interest and the ultrasound probe. The ultrasound image includes the site of interest and a plurality of tissue regions in the pass zone. Boundaries of a selected tissue region in the pass zone are determined from the image. Respective focusing delay times for each transducer element associated with an ultrasound beam passing through the selected tissue region are computed. The focusing delay times are computed based, at least in part, on a speed of sound in the selected tissue region other than an average speed of sound in body tissue, and the determined boundaries of the selected tissue region. An ultrasound imaging scan of the pass zone is then conducted employing the computed focusing delay times.

The focusing delay times may be computed by determining a respective propagation time between each transducer element and respective points in the pass zone based, at least in part, on the speed of sound in the selected tissue region other than the average speed of sound, and a respective distance traveled by an ultrasound beam through the selected tissue region, based on the determined boundaries. Refraction of the ultrasound beams may be considered in computing the focusing delay times.

The speed of sound in the selected tissue region other than an average speed of sound in body tissue is preferably "about" the speed of sound in the tissue type of the selected tissue region. In the present application, what is considered "about the speed of sound" varies for different tissue types. For example "about the speed of sound" in fat tissue is a speed within a range of plus or minus 3% of 1460 m/s. More preferably, the speed is in a range of plus or minus 1% of 1460 m/s. Most preferably, the speed of sound in fat tissue of 1460 m/s is used. For muscle tissue, "about the speed of sound" is a speed in a range of plus or minus 2% of the speed of sound of 1600 m/s. More preferably, the speed is in a range of plus or minus 1% of 1600 m/s and even more preferably, the speed of sound in muscle tissue of 1600 m/s is used. For liver tissue and kidney tissue, "about the speed of sound" are speeds in ranges of plus or minus 2.0% of the speeds of sound of 1555 m/s and 1565 m/s, respectively. More preferably, the speeds are in a range of plus or minus 1.0%, and more preferably plus or minus 0.5% of 1555 m/s and 1565 m/s, respectively. Most preferably, the speeds of sound of 1555 m/s and 1565 m/s are used for liver tissue and kidney tissue, respectively. For bone tissue, "about the speed of sound" is a speed in a range of plus or minus 40% of 3000 m/s. More preferably, the speed is within a range of plus or minus 20% of 3000 m/s. A speed in a range of plus or minus 10% of 3000 m/s is even more preferred, and most preferably, 3000 m/s is used. The speed of sound in brain tissue has been observed to be about 1570 m/s. For brain tissue, "about the speed of sound" is a speed in a range of plus or minus 3% of 1570 m/s. A speed in a range of plus or minus 1.0% of 1570 m/s may also be used. 1570 m/s may be used as well.

The selected tissue region may be a fat, bone, muscle and/or organ tissue region. As mentioned above, sufficient correction may generally be obtained by selecting fat and bone tissue regions, if present. Further correction may be obtained by using the speed of sound in muscle tissue, instead of the average speed of sound in body tissue for non-selected soft tissue regions. Even further correction may be provided by determining the boundaries of muscle and organ tissue regions, if present, and considering the speeds of sound in those tissue regions, as well.

The focusing delay times may be transmission delays, which are computed for each transducer element transmitting an ultrasound beam through the selected tissue region. Each transmission delay is computed such that ultrasound beams transmitted by respective transducer elements will constructively interfere at a selected focal point.

The computed focusing delay times may also be reception delays, which are computed for each transducer element receiving an ultrasound beam passing through the selected tissue region. The reception delays are computed such that ultrasound beams reflected from reflecting bodies in the pass zone are in phase after detection.

The focusing delay times may be computed, at least in part, by conducting a ray calculation between a point in the pass zone and each transducer element transmitting an ultrasound beam through, and/or receiving an ultrasound beam passing through, the selected tissue region. A distance traveled in the selected tissue region for each ultrasound beam corresponding to a ray may then be determined.

The ultrasound image may be obtained from an ultrasound imaging scan employing initial focusing delay times based on an average speed of sound in body tissue. The respective computed transmission and or reception delays may also be computed by determining a respective adjustment to the initial focusing delay times for each transducer element transmitting or receiving an ultrasound beam passing through the selected tissue region. The adjustments may be based, at least in part, on a phase shift for each ultrasound beam, caused by passage through the selected tissue region.

The boundaries of the selected tissue region may be determined by segmentation. A three dimensional boundary of the selected tissue region may be determined based on a plurality of ultrasound images of the pass zone, where each image comprises a different sectional plane through the site of interest. Three dimensional boundaries of the selected tissue region may also be determined by three dimensional ultrasound imaging of the pass zone.

If the initial correction process does not provide sufficient improvements in image contrast resolution, the process may be repeated using the corrected image resulting from an ultrasound imaging scan employing the computed focusing delay times. The corrected image may be used to determine the boundaries of the selected tissue region, which are then used to compute new focusing delay times for a subsequent corrected image. The process may be repeated any number of times with each subsequent corrected image. Each corrected image should be an improvement over the prior image.

In accordance with other embodiments of the invention, an ultrasound imaging system, software stored on a machine readable medium for controlling an ultrasound imaging system and a method for determining focusing delays, are also disclosed.

In accordance with yet another embodiment of the invention, an ultrasound probe comprising high and low frequency transducers is also disclosed.

DETAILED DESCRIPTION OF THE INVENTION

Figure 1:
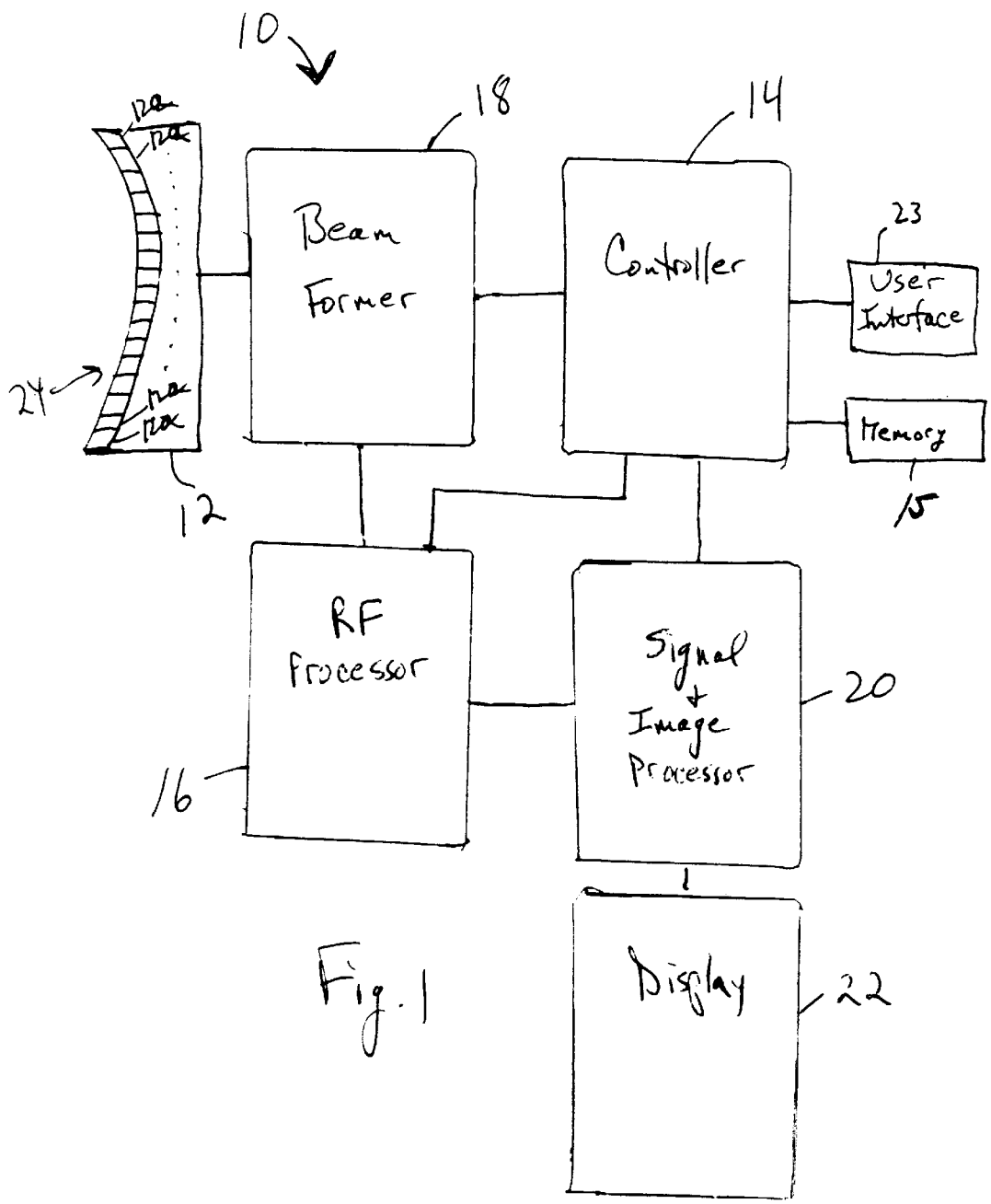
FIG. 1 is a schematic representation of an ultrasound imaging system in accordance with one embodiment of the invention.

FIG. 1 is a schematic representation of an ultrasound imaging system 10 comprising an ultrasound probe 12, a controller 14, a Radio Frequency ("RF") processor 16, a beam former 18, a signal and image processor 20 and a display 22, in accordance with one embodiment of the invention. The ultrasound probe comprises a plurality of ultrasound transducer elements 12a. The controller 14 controls the operation of the system 10, in accordance with software stored in a memory device 15. The controller 14 is coupled to the RF processor 16, the beam former 18 and the signal and image processor 20 to provide signals for controlling the transmission, detection and processing of ultrasound beams.

The beam former 18 has an output coupled to an input of the ultrasound probe 12, to provide driving signals with appropriate transmission delays to the transducer elements 12a of the probe. Echo signals detected by the transducer elements are converted into electrical signals and provided to the beam former 18, which applies appropriate reception delays to each signal. The signals are then summed by the beam former 18. The RF processor 16 has an input coupled to an output of the beam former 18 to receive the summed signals for further processing, as is known in the art. The signal and image processor 20 has an input coupled to an output of the RF processor 16 to receive the processed signals for further processing and reconstruction, as is known in the art. The processor 20 provides the reconstructed signals to the display 22. The functions of the RF processor 16 and the signal and image processor 20 may be performed by a single processor.

One or more user interface devices 23 may also be provided in the system 10, with outputs coupled to an input of the controller 14. The user interface device 23 may comprise a trackball and/or a keyboard, for example. A user interface device may be coupled to the signal and image processor 20, as well.

The ultrasound probe 12 typically comprises a transducer array 24 of ultrasound transducer elements 12a. The transducer array 24 may be a single row or a matrix of transducer elements 12a. The transducer array 24 may be curved, as shown in FIG. 1, for placement on a subject's skin. The transducer array 24 may also be planar, parabolic, or any other suitable shape. The transducer elements 12a of the transducer array 24 may be piezoelectric transducer elements, such as piezoelectric ceramic pieces mounted in silicone rubber or any other material suitable for damping the mechanical coupling between the elements. Other materials may also be used for the array construction. For example, the transducer array 24 may be formed from one or more pieces of piezocomposite material, or any material that converts electrical energy to acoustic energy.

The beam former 18 is a control and processing device that may also comprise a frequency generator. Alternatively, a separate frequency generator may be coupled to the beam former 18, as well. As discussed above, the beam former 18 imposes suitable transmission delays on each driving signal, so that the ultrasound beams transmitted by each transducer element 12a constructively interfere at one or more focal points selected by an operator of the ultrasound imaging system 10, proximate the site of interest. The controller 14 typically computes the required transmission delays by calculating the propagation time from each transducer element 12a to a focal point, assuming that the speed of sound is an average speed of sound in body tissue, or other uniform value, through all the tissue regions in the pass zone between each transducer element 24 and the focal point.

The beam former 18 also receives echo signals detected by the transducer elements 12a from tissue and other reflecting bodies in the pass zone. The beam former 18 applies suitable reception delays to the echo signals and sends the signals to the RF processor 16 and the signal and image processor 20 for reconstruction and display on the display 22. The reception delays for the echo signals are typically computed by the controller 14 based on the propagation time for an ultrasound signal reflected from a plurality of points at varying depths in the pass zone, and the average speed of sound in body tissue. For example, reception delays may be computed for 100 to 200 different depths in the pass zone. Transmission of ultrasound beams and reception of echo signals are alternated, under the control of the controller 14, as is known in the art. The beam former 18 may perform these computations instead of the controller 14. The beam former 18 may include the controller 14, as well.

The controller 14 performs processing, logic and timing functions related to the operation of the ultrasound imaging system 10. The controller functions may be provided by software, hardware, firmware, hardwiring, or combinations of any of these. For example, the controller 14 may be a general purpose, or special purpose, digital data processor or computer programmed with software in a conventional manner in order to calculate focusing delay times for use by the beam former 18 in accordance with the embodiments of the present invention, as discussed below. The memory 15 may be a magnetic, optical or semiconductor memory device, including, without limitation, read only memory ("ROM"), including DVD ROM, or random access memory ("RAM"), including DVD RAM. The memory 15 may be the hard drive of a computer. The software may be provided on a machine readable medium, such as a CD-ROM or a floppy disk, for example. The software may also be downloaded from a server via the Internet.

Figure 2:
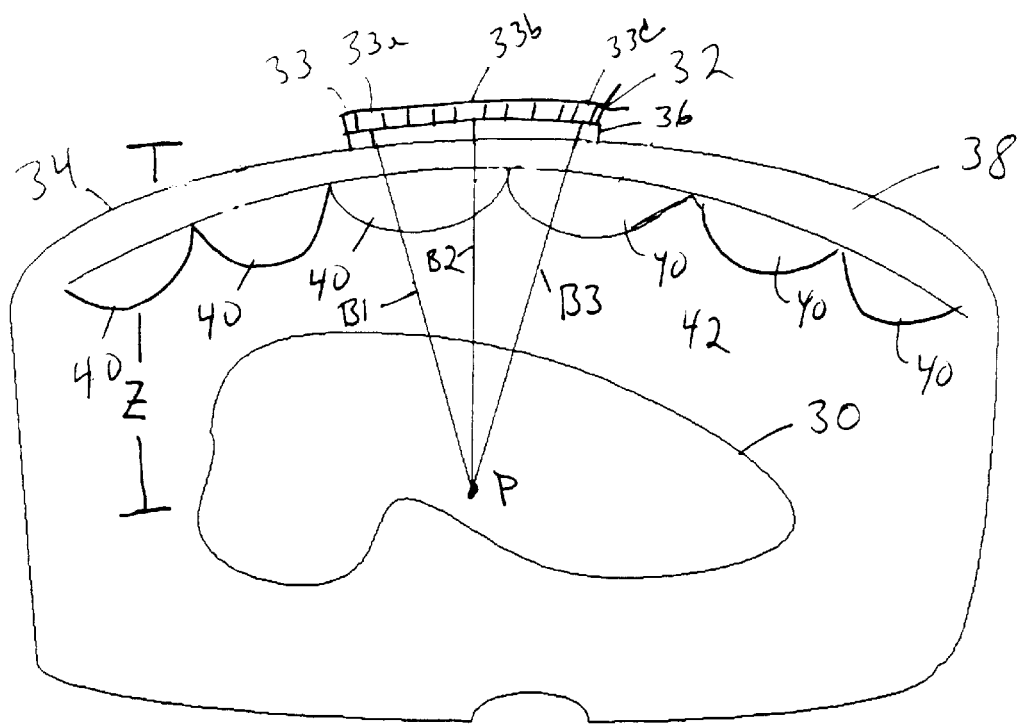
FIG. 2 is a cross-sectional view of a portion of a patient's anatomy including a site of interest for ultrasound imaging.

FIG. 2 is a cross-sectional view of a portion of a patient's anatomy including a site of interest 30 for ultrasound imaging. In this example, the site of interest 30 is an organ, such as the liver. A transducer array 32 comprising a plurality of transducer elements 33 is shown adjacent to the patient's skin 34, aligned with the site of interest 30. A coupling medium 36, such as an ultrasound gel, is typically provided between the transducer array 32 and the skin 34, to improve coupling of ultrasound energy between the subject's body and the transducer array 32. The thickness of the coupling medium 36 is shown exaggerated in FIG. 2 for illustrative purposes. Regions of different tissue types in a pass zone Z between the patient's skin and the site of interest 30 are shown. In this example, below the skin 34, there is a layer fat 38. Below the fat layer 38 are muscle tissue regions 40. Between the muscle tissue regions 40 and the site of interest 30 is another layer of fat 42.

Three exemplary ultrasound beams B1, B2, B3 are shown being transmitted from three transducer elements 33a, 33b, 33c in the transducer array 32, focused on a focal point P within the site of interest 30. In actual imaging, all of the transducer elements 33 are driven to transmit ultrasound beams focused on the focal point P. Additional focal points may be provided as well, but that may slow the imaging process. The beams B1, B2, B3 pass through the first fat region 38, one of the muscle regions 40, the second fat region 42 and part of the organ tissue of the site of interest 30, as they travel to and from the focal point P.

As mentioned above, in conventional ultrasound imaging, the transmission delays introduced to the ultrasound beams B1, B2, B3 by the beam former 18 (shown in FIG. 1) are based on the uniform and average speed of sound in body tissue of 1540 m/s (or other such uniform speed considered to be an average speed of sound in body tissue), and the distance from each transducer element 33a, 33b, 33c to each focal point P. However, during transmission, the differing speeds of sound in each tissue type in the pass zone Z shift the expected phase of each beam at the focal point P. The desired constructive interference at the focal point P is decreased and destructive interference is increased, degrading image contrast resolution. Similarly, reception delays for reception of echo signals are also conventionally computed using the same speed of sound as is used in computing the transmission delays. The phase alignment of the echo signals is also therefore shifted, further degrading the image. In addition, geometrical errors in the location of objects in the image may be introduced.

In accordance with an embodiment of the invention, delay times for each ultrasound transducer element of an ultrasound probe for focusing ultrasound beams during transmission and/or reception, are determined based in part on a speed of sound other than the average speed of sound in body tissue. Preferably, the speed of sound is the actual speed of sound through one or more of the tissue regions traversed by each ultrasound beam to and from the focal point P and reflecting bodies in the pass zone Z. In a preferred embodiment, the speed is used in conjunction with the distance each ultrasound beam traverses each region to compute the new delay times, which are used in subsequent ultrasound imaging scans to obtain corrected ultrasound images. The constructive interference of transmitted ultrasound beams at the focal point P and other focal points, if present, is thereby improved. The phase alignment of echo signals is also improved. The contrast resolution of the corrected ultrasound images is thereby improved.

Figure 3:
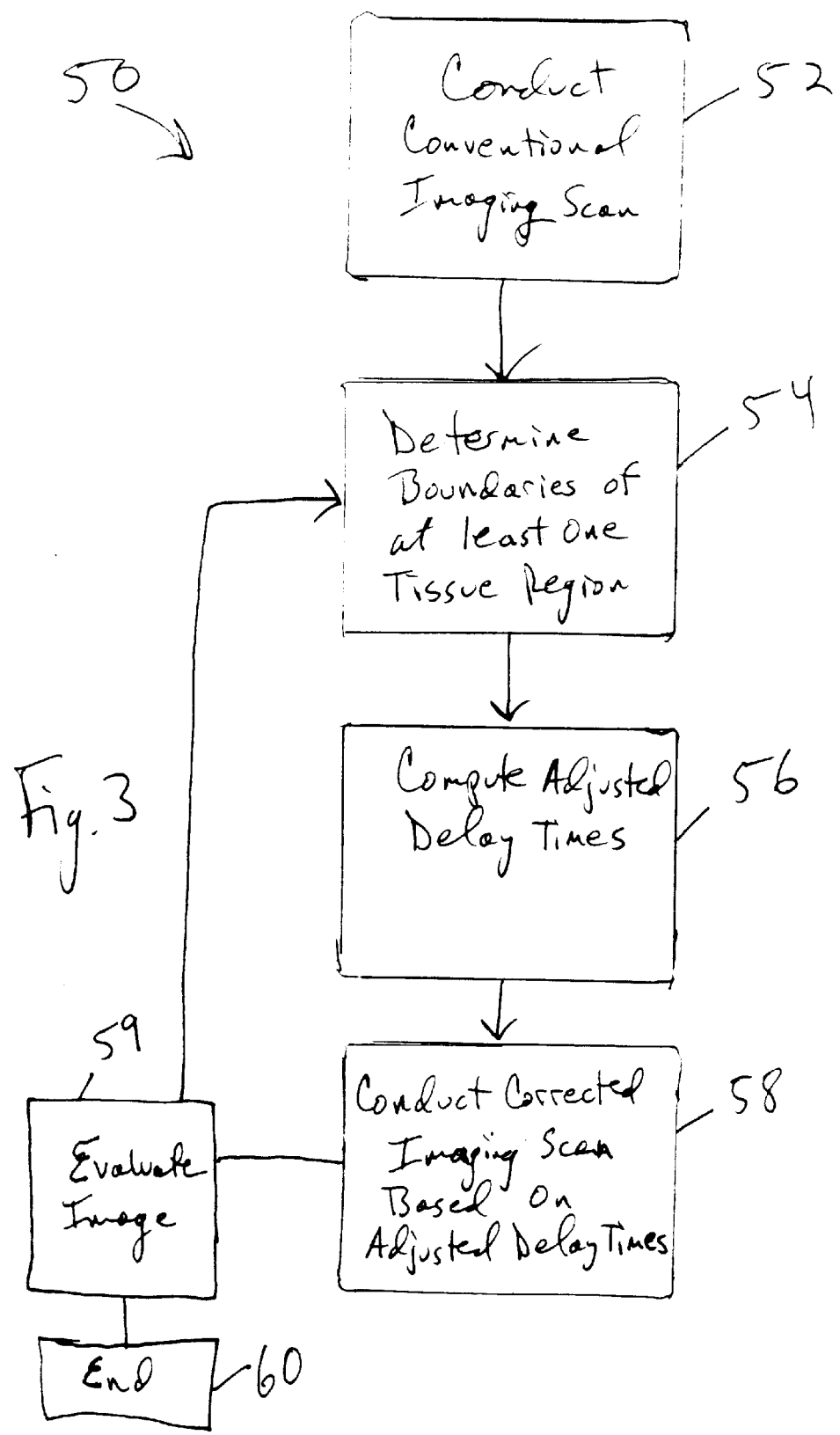
FIG. 3 is a flow chart of an imaging method in accordance with one embodiment of the invention.
Figure 4:
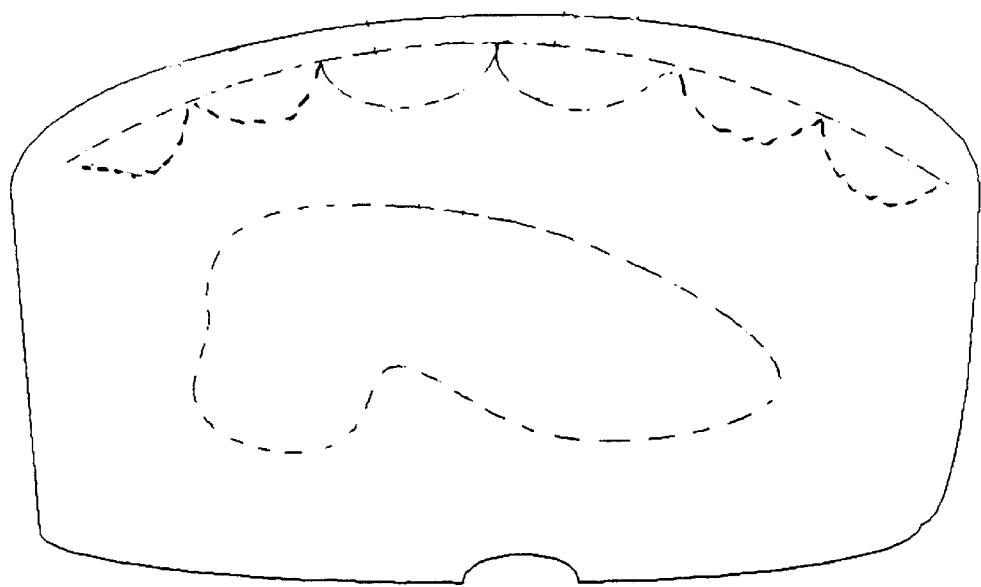
FIG. 4 is a schematic representation of an ultrasound image of the portion of the patient's anatomy of FIG. 2.

FIG. 3 is a flow chart of an ultrasound imaging method 50 in accordance with one embodiment of the present invention. In step 52, conventional ultrasound imaging is conducted of a site of interest, wherein delay times are computed for each of the transducer elements 33 of the transducer array 32 using an average and uniform speed of sound through tissue of 1540 m/s, or another such average and uniform value, for transmission and reception of ultrasound beams. One or more two dimensional sectional planes including the site of interest may be imaged. Alternatively, a three dimensional volume including the site of interest may be imaged. The results of the conventional imaging may be reconstructed by the signal and image processor 20 and displayed on the display 22 of the ultrasound system 10, or another computer system, in a conventional manner. A-mode or B-mode images may be reconstructed, for example. FIG. 4 is an example of a schematic representation of a resulting image.

The boundaries of at least one tissue region in the pass zone Z (see FIG. 2) are then determined on the image or images resulting from the initial ultrasound imaging scan, in step 54. In this example, all the tissue regions on the pass zone Z are therefore segmented.

The boundaries of the tissue regions may be determined in step 54 by segmentation. During segmentation, the boundaries are defined. Every voxel in the segmented volume is automatically mapped into a pass zone data set and correlated to a tissue type. Each voxel is assigned coordinates identifying its location in space ((X, Y) for a two dimensional data set and (X, Y, Z) for a three dimensional data set) and its tissue type (T), resulting in a data set comprising (X, Y, T) or (X, Y, Z, T) coordinates for each voxel. Tissue type may be manually entered or automatically determined by an algorithm, as is known in the art.

Segmentation may be performed in a variety of manual, semi-automatic and automatic methods. For example, a human operator may manually segment one or a plurality of the images of the two dimensional sectional planes by tracing boundaries between one or more tissue types on each image 54 with a suitable interface device 23 (See FIG. 1), such as a pointer controlled by a mouse. A three dimensional volume of the pass zone Z may be interpolated from a sufficient number of segmented two dimensional images, if desired. The number of two dimensional images used to interpolate a three dimensional volume is dependent on the geometrical rate of change of the tissue region in the pass zone Z and the desired accuracy of the interpolation.

In a semi-automatic segmentation technique, an expanding area algorithm is implemented by the signal and image processor 20 to fill each region of the image or images designated by a user with the interface device 23. For example, clicking on a mouse while a pointer is within a region of an image can cause execution of the expanding area algorithm to automatically fill the selected region. Other types of algorithms may be used, as well.

A segmentation algorithm implemented by the signal and image processor 20 may also be used to automatically segment each tissue region. Automatic or semi-automatic segmentation would be used to directly segment a three dimensional volume image.

Figure 5:
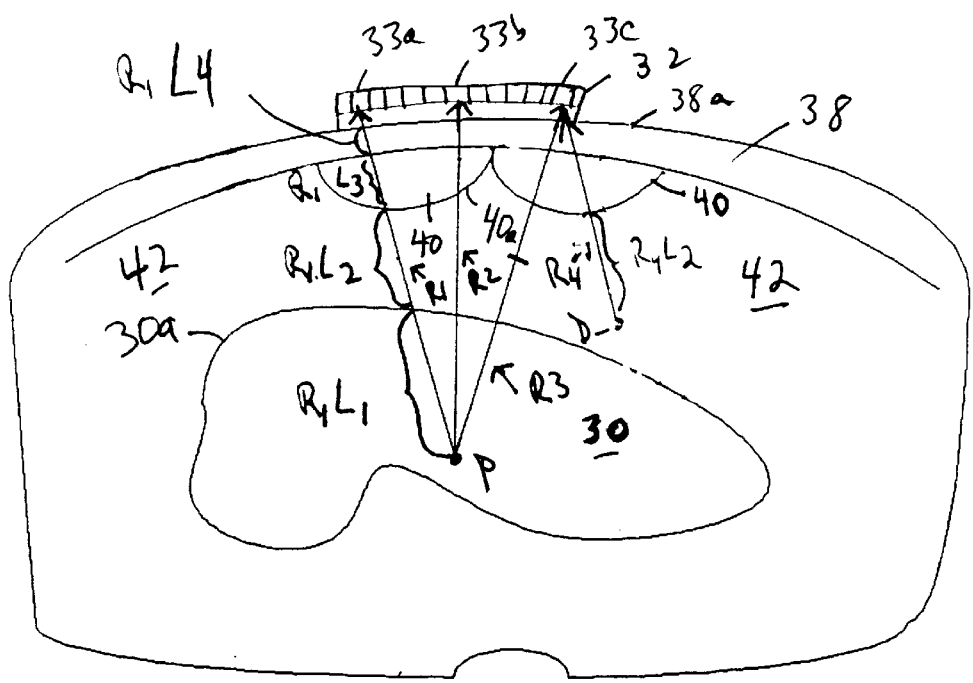
FIG. 5 shows a partially segmented version of the image of FIG. 4.

FIG. 5 shows a segmented version of the image of FIG. 4, wherein the boundaries of the first fat region 38, the boundaries of two of the muscle regions 40, the second fat region 42 and the organ tissue of the site of interest 30 have been determined.

Delay times for each transducer element 33 for use in transmission and reception focusing are then computed based, at least, in part on the speed of sound through the one or more segmented tissue regions and the boundaries of the those regions, in step 56. The boundaries may be used to determine the distance traveled by each beam through each tissue region. The distance traveled in each region may be determined by the controller 14 or the signal and image processor 20 under software control, using a ray calculation, for example. A reverse ray calculation or a forward ray calculation between each transducer element 24 and the reflector depths may be performed.

FIG. 5 shows how a reverse ray calculation may be performed on the segmented image of FIG. 4 from the focal point P to three of the transducer elements 33a, 33b, 33c. The controller 14 or the signal and image processor 20 compute rays R1, R2, R3 from the focal point P to each of the transducer elements 33a, 33b, 33c. (In a forward ray calculation, the rays are drawn from each transducer element 33 to the focal point P.). The rays correspond to the ultrasound beams B1, B2, B3 in FIG. 3, respectively. For the first ray, R1, a distance R1L1 of the ray segment extending from the focal point P within the organ 30 to the boundary 30a between the organ 30 and the adjacent tissue type, here the fat region 42, is determined. The distance R1L1 may be computed by identifying the voxel coordinates on the boundary that the beam traverses. If the focal point P has voxel coordinates (Xp, Yp, Zp) and the boundary has voxel coordinates (Xq, Yq, Zq), then the distance R1L1 between them is:

$$((Xp-Xq)^2+(Yp-Yq)^2+(Zp-Zq)^2)^{1/2} \quad (1)$$

The distances R1L2, R1L3 and R1L4 of the respective ray segments through the second fat region 42, the muscle region 40 and the first fat region 38, respectfully, may be similarly computed based on the voxel coordinates of the boundaries 40a, 38a between the respective regions traversed by the beam B1.

The propagation time TR1L1 of the beam B1 through the region L1 is:

$$T_{R1L1} = \frac{R1L1}{V} m/s, \quad (2)$$

where V is the speed of sound through the organ tissue (1555 m/s for liver tissue, for example).

The propagation times may be similarly computed for the ultrasound beam B1 through the other tissue regions based on the ray segments R1L2, R1L3 and R1L4, where V is the speed of sound in fat tissue (1460 m/s), muscle tissue (1600 m/s) and fat tissue, respectively. The propagation times for the ultrasound beam B1 through each tissue region is summed to yield an adjusted propagation time for the ultrasound beam B1. Propagation times for the other ultrasound beams B2, B3, and the ultrasound beams transmitted by each of the other transducer elements 33 of the transducer array 32 to the focal point P, are computed in a similar manner. The adjusted propagation times for each transducer element 33 is then used by the controller 14 to determine adjusted transmission delays for each ultrasound beam transmitted by each transducer element 33, in step 56.

Reception delays for processing the echo signals from the pass zone Z are also similarly computed, based on selected depths in the pass zone. FIG. 5 also shows a ray R4 extending from one of a plurality of points D in the pass zone Z to the transducer element 33c. To determine an adjusted delay time for an echo signal reflected from tissue or other such reflecting body at point D to the transduce r element 33c, the propagation time for the ultrasound beams traveling from the point D to the transducer 33c is determined. A ray R4 is drawn and its length in the fat tissue region 42 is determined based on the voxel coordinates at the point D and the voxel coordinates of the boundary between the fat tissue region 42 and the muscle tissue region 40, by equation (1), above. The propagation time TR4L2 in the fat tissue region 42 is then determined by equation (2), above. The propagation times for the ultrasound beam traveling along the ray R4, through the tissue regions 40 and 38, are similarly computed. The propagation times are summed and used to compute an adjusted reception delay for an echo signal reflected from the point D to the transducer element 33c. Rays are similarly drawn from the point D to each of the other transducer elements 33 and adjusted delay times are similarly computed. Adjusted reception delays may b e computed at 100 to 200 points along the ray from the focal point P to each ultrasound element 33.

In computing the transmission and reception delays, a speed that is "about" the speed in the respective tissue region is preferably used. The closer the speed is to the actual speed of sound in a particular body tissue, the better the improvements in contrast resolution due to the correction for tissue inhomogeneity. As used herein, the term "about the speed of sound" for fat tissue is a speed in a range of plus or minus 3% of the speed of sound of 1460 m/s. A speed in a range of plus or minus, 1% of 1460 m/s is preferred. The speed of 1460 m/s is most preferred. For muscle tissue, "about the speed of sound" is a speed in a range of plus or minus 2% of 1600 m/s. A speed in a range of plus or minus 1% of 1600 m/s is preferred and the speed of 1600 m/s is more preferred. For liver and kidney tissue, "about the speed of sound" are speeds in ranges of 2.0% of the speeds of 1555 m/s and 1565 m/s, respectively. Speeds in ranges of plus or minus 1.0% of the respective speeds are more preferred. Speeds in ranges of plus or minus 0.5% of the respective speeds are even more preferred and the speeds of 1555 m/s and 1565 m/s for liver and kidney tissue are most preferred. For bone tissue, "about the speed of sound" is a speed in a range of plus or minus 40% of the speed of 3000 m/s. A speed in a range of plus or minus 20% of 3000 m/s is preferred, a speed in a range of plus or minus 10% of 3000 m/s is more preferred and the speed of 3000 m/s is most preferred. The speed of sound in brain tissue has been observed to be about 1570 m/s. A speed of "about the speed of sound" for brain tissue is in a range of plus or minus 2.0% of 1570 m/s. A speed in a range of plus or minus 1.0% of 1570 m/s may be used. 1570 m/s may be used, as well.

A new, corrected ultrasound imaging scan is conducted in step 58 employing the adjusted delay times. The corrected image is evaluated in step 59 by the signal and image processor 20, the controller 14 or visually. If the image has sufficient contrast resolution, the process is completed (step 60).

If the image does not have sufficient contrast resolution, the tissue aberration correction may not have been sufficient. This may be due to inaccuracies in the initial ultrasound image used for segmentation in step 54, due to tissue inhomogeneities. While generally the segmented boundaries of the initial image will be accurate enough to compute sufficiently improved propagation times, that might not always be the case. Step 54 may then be conducted again based on the corrected image. The segmented boundaries on the corrected image should be more accurate then the segmented boundaries on the initial image.

Adjusted delay times are computed again in step 56 and employed in conducting another corrected ultrasound imaging scan in step 58. The twice corrected image is evaluated again in step 59. If sufficient, the process may be ended. If still not sufficient, step 54 may be conducted again on the twice corrected image. This process may be repeated until an adequate image is generated.

Contrast resolution problems may also be due to deviations from the actual speed of sound in particular tissue regions in certain individuals. Improving the accuracy of the segmented boundaries by repeating steps 54, 56 and 58 with corrected images will generally provide sufficient improvements in contrast resolution despite such deviations.

In the example above, each tissue region in the pass zone was segmented and the actual speed of sound in that tissue type was used in conjunction with the distance traveled by each ultrasound beam in that tissue type, to compute the adjusted delay times. While providing a high level of improvement in contrast resolution, that is not always necessary. The difference between the speed of sound though fat tissue (1440 m/s) and the average speed of sound in body tissue (1540 m/s) is about 6.5%, which may cause considerable phase shifts that can seriously degrade contrast resolution. The speed of sound in muscle tissue (1600 m/s) is about 4.0% faster than the average speed of sound in body tissue, which may cause some phase shifts that can also decrease contrast resolution. Among organ tissues, the speed of sound in the liver is 1555 m/s, which is about 1.0% faster than the average speed of sound of 1540 m/s. The speed of sound in a kidney is 1565 m/s, which is about 2.0% faster than the average speed of sound in body tissue of 1540 m/s. Such small deviations from the average speed of sound would only cause small or negligible phase shifts that may be ignored except where the highest contrast resolution is desired.

In addition, certain of the speed ranges for different tissue types recited above overlap portions of the range of the average speed of sound in body tissue of 1540 m/s plus or minus 3%. Where an average speed of sound in body tissue is used that is within about 4% of the speed of sound in a particular tissue type, the average speed of sound in body tissue may be used to determine the propagation time through that tissue region, at least initially.

The tissue aberration correction process in ultrasound imaging of a pass zone containing only soft tissue may be simplified by only segmenting the fat tissue region or regions in the pass zone and only determining the distances traveled by each ultrasound beam in the segmented regions. The distance traveled in the segmented region may then be subtracted from the total distance traveled by the respective ultrasound beam between the transducer element 33 and the focal point P, which is usually known within acceptable tolerances, to determine the distance traveled in the remaining soft tissue regions. The average speed of sound in body tissue may be used to determine the propagation time in the remaining soft tissue. If that does not yield an adequate image, additional improvement in the correction and hence further improvements in contrast resolution may be obtained by repeating step 56 using the speed of sound in muscle tissue to determine the propagation time in the remaining soft tissue regions. If that still does not yield an adequate image, each tissue region may be segmented and the different speeds of sound in those tissue regions may be considered, as well. Step 56 may be repeated with the same initial image, or with a currently corrected ultrasound image derived from the partial correction, as discussed above.

The software controlling the tissue aberration correction method may be designed to conduct only one type of analysis or allow for an operator to choose among the options.

The speed of sound through bone tissue (3000 m/s for skull bone tissue, for example), is much faster than the average speed of sound in body tissue, resulting in significant phase shifts and resulting loss in contrast resolution. It would therefore be advantageous to segment bone tissue regions and use the actual speed of sound in bone tissue to determine the propagation time of the ultrasound beams traversing bone tissue. The other soft tissue regions in the pass zone may be dealt with by segmenting each tissue region in the pass zone or following one of the simplified methods discussed above. (We note that the speed of sound in skull bone is sometimes quoted as 4080 m/s. While that or some other value may be used, we have found the value of 3,000 m/s to be more accurate).

Tissue inhomogeneity can also cause refraction that can alter the path, and hence the distance traveled by the ultrasound beam in each tissue region. The phase of the transmitted ultrasound beams at the focal point and the phase of the echo signals received by the transducer elements may thereby be further shifted, further degrading the contrast resolution of the resulting ultrasound images. After determining the boundaries of the selected tissue region in step 54, the effects of refraction of the beams as the beams enter each tissue region may also be considered in determining the adjusted focusing delay times for further improvements in contrast resolution in step 56.

Ultrasound beam refraction is described by Snell's law:

$$\frac{\sin\theta_1}{\sin\theta_2} = \frac{C_1}{C_2} \quad (3)$$

where $\theta_1, \theta_2$ are the angles between the normal to the surface and the incident and refracted rays in the respective tissue regions and $C_1, C_2$ are the speeds of sound in the respective tissue regions. As mentioned above, the impact of refraction between soft tissues on contrast resolution is generally limited. However, refraction at the boundary between soft tissue and bone may be more significant. Consideration of refraction to correct tissue aberration may be particularly useful in ultrasound imaging of the brain. The ray calculations described above may be readily modified to take into account refraction of the ultrasound beams.

Figure 6:
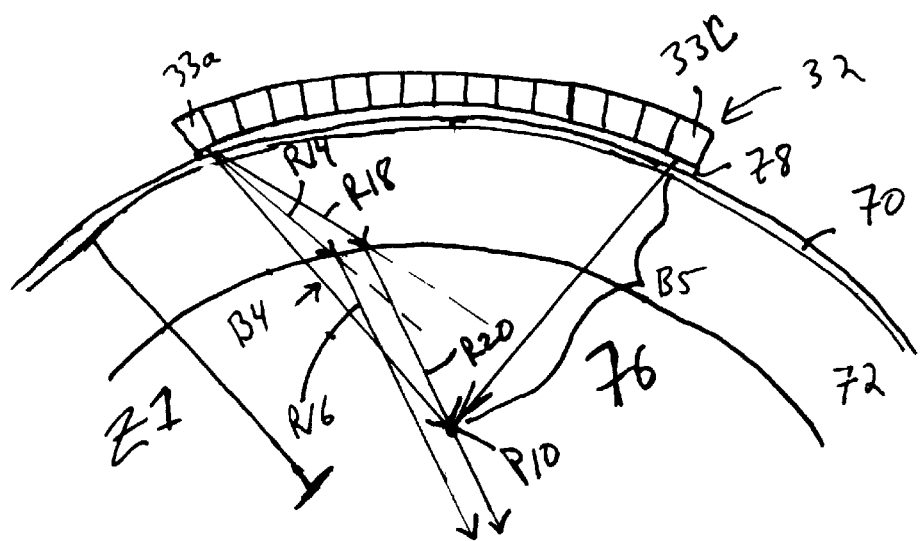
FIG. 6 is a segmented ultrasound image of a portion of a subject's brain, showing refraction of transmitted ultrasound beams.

FIG. 6 is a segmented ultrasound image of a pass zone Z1 between the transducer array 32 and a site of interest within a patient's brain. A layer of coupling material 78 is shown between the transducer array 32 and the skin 70, as discussed above.

The speed of sound in brain tissue is about 1540 m/s. The transducer array 32 is shown adjacent to the skin 70 and the skull bone tissue 72 for imaging brain tissue 76. The skull bone tissue 72 typically comprises two layers of cortical bone with a layer of trabecular bone in between. Trabecular bone and cortical bone have different densities, which will vary the speed of sound. As a first approximation, the skull bone tissue may be considered to be homogenous and an average speed of sound in skull bone tissue of 3000 m/s may be used for the entire bone tissue region 72. Alternatively, the multiple layers of bone tissue may be segmented and the speeds of sound and the distance traveled in each segmented region may be separately considered in accordance with the teachings of the present invention, if desired or found to be necessary for further improvements in the contrast resolution.

First and second ultrasound beams B4, B5 are shown being transmitted by transducer elements 33a, 33c at opposite ends of the transducer array 32, focused on a focal point P10, assuming that there is no refraction. Ray R14 shows the effect of refraction on the beam B4 due to the interface between the bone tissue region 72 and the skin 70. The ray R16 shows the effect of refraction on the ray R14 at the interface between the bone tissue region 72 and the brain tissue region 76. Because of refraction, the beam B4 does not intercept the focal point P10.

In order to conduct a ray calculation to determine propagation times for ultrasound beams transmitted by each transducer element, ray segments R18, R20 need to be generated by the controller 14 between the first transducer element 33a and the focal point P10, as either forward rays drawn from the transducer element 33a to the focal point P10 or reverse rays drawn from the focal point P10 to the transducer element 33a on a segmented image. The lengths of the ray segments R18, R20 may be determined based on the coordinates of the boundaries of the segmented tissue regions intercepted by the rays through Equation 1, above. The propagation times for ultrasound beams traveling the lengths of the ray segments R18, R20 are determined through Equation 2, above. Preferably, the speed of sound in bone tissue of 3000 m/s is used with the ray segment R18. The speed of sound in brain tissue of 1540 m/s is preferably used with the ray segment R20. While the speed of sound in brain tissue is the same as the average speed of sound in body tissue, a new propagation time for the ray segment R20 needs to be computed because the refraction of the ray changes the distance traveled. The propagation times are summed to obtain a total propagation time for use in computing a transmission delay in step 56. Ray segments may be similarly generated and transmission delays similarly computed for ultrasound beams transmitted by all the other transducer elements 33. (It is noted that ultrasound beams transmitted by a transducer element that is normal to a boundary of a tissue region will not be refracted by the boundary.). Reception delays are similarly computed to take refraction into account, as well.

After the adjusted transmission and reception delays are computed, including consideration of refraction in step 56, a new ultrasound imaging scan is conducted in step 58 employing the adjusted delay times to obtain a corrected image. Because of inaccuracies in the segmented boundaries in the initial ultrasound image due to the degraded contrast resolution, the initial refraction corrected ultrasound beams may miss the actual focal point P10 by more than an acceptable tolerance. If the refraction corrected ray is outside a predetermined tolerance, which may be determined by the controller 14 or the signal and image processor 20, or the corrected image itself does not appear to have sufficient contrast resolution, the corrected ultrasound image may be segmented in step 54 and the adjusted delay times calculated again in step 56. As above, the corrected ultrasound image will provide some correction for tissue inhomogeneities that will enable improved segmentation. The twice refraction and inhomogeneity corrected ultrasound beams should therefore provide better aberration correction than the first set of refraction and inhomogeneity corrected ultrasound beams. The decision to iterate the phase aberration correction, e.g. segmenting the corrected image 54 and re-computating the adjusted delays 56, could be based on the change in the phase aberration values between two consecutive iteration steps. As an example, iteration of steps 54–59 may be stopped when the change is less than ±5% of the previous step correction. Another possible criteria for stopping iterations could be frequency content in a predefined bandwidth in the resulting image.

Refraction correction is preferably performed if bone tissue is present in the pass zone. Where only soft tissue is present in the pass zone, the refraction correction is optional. The controller 14 may be programmed to enable selection of refraction correction by an operator, depending on whether bone tissue is present. In addition, if the embodiment of method 50 is implemented on soft tissue without refraction correction of the delay times in step 56, and the resulting corrected image is not adequate, step 54 may be repeated with the corrected ultrasound image and refraction correction may be included in step 56.

Figure 7:
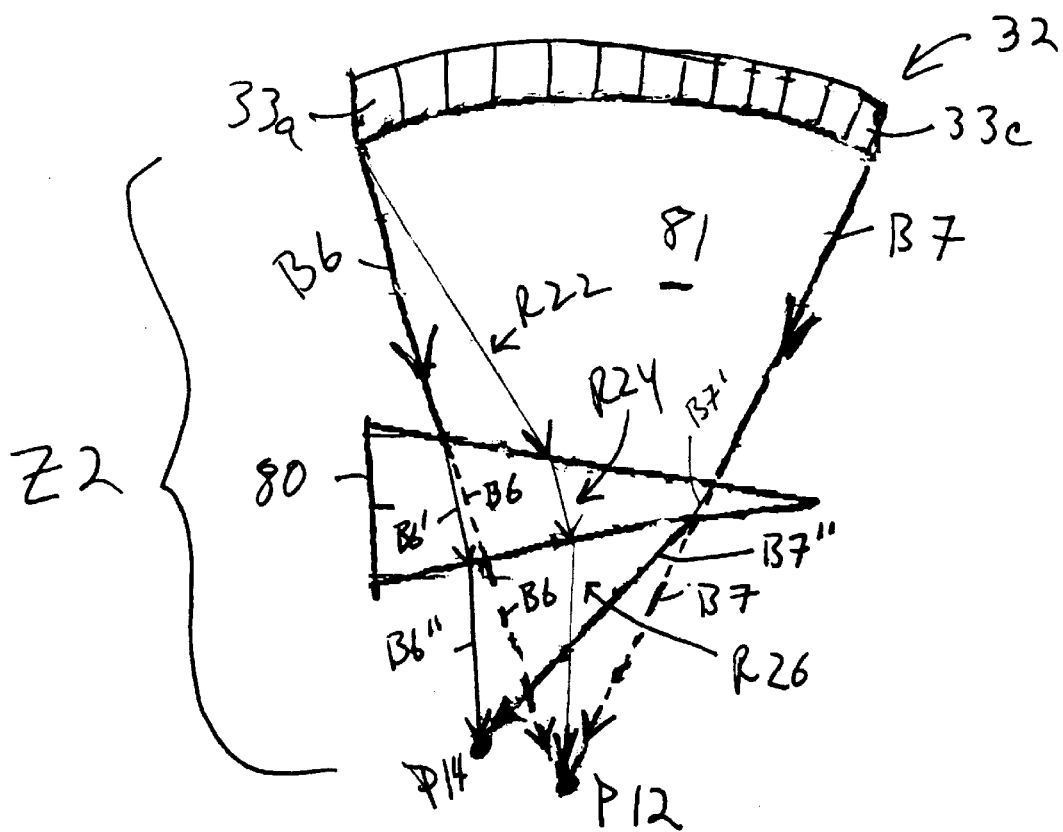
FIG. 7 is a schematic representation of refraction caused by a prism shaped tissue region.

Depending on the shape of a tissue region, the constructive interference at the focal point may not be appreciably degraded. FIG. 7 shows the transducer array 32 of FIG. 5 and a segmented fat tissue region 80 in a pass zone Z2. The tissue 81 between the transducer array 32 and the fat tissue region 80 is assumed to be muscle tissue. Other tissue regions in the pass zone Z2 are not shown to simplify the view. The segmented tissue region 80 has a uniformly changing thickness across a plane containing the transducer array 32. The rate of change of depth with distance is monotonic (continuously increasing or decreasing) and linear (the boundary may be defined by the equation Y=a+bx). Such a tissue region may be modeled as a prism.

Two exemplary ultrasound beams B6, B7 are shown being transmitted from the two transducer elements 33$a$, 33$c$ on opposite sides of the transducer array 32. The beams B6, B7 are intended to be focused on a focal point P12 selected by an operator of the ultrasound imaging system 10. However, refraction causes the two ultrasound beams B4, B5, and all the other ultrasound beams transmitted by the transducer elements 33, to be focused on a new focal point P14 at a different position than the selected focal point P12. The refracted beams B6, B7 are indicated, partially in solid lines and partially in dotted lines. The actual paths of the beam B6, B7 through the prism are indicated by solid lines B6', B6", B7', B7". While shifting the position of the focal point P12 in space, because of the shape of the tissue region 80, the desired degree of constructive interference at the focal point is within acceptable tolerances.

Shifting the position of the focal point may introduce geometric errors in the positions of objects in the ultrasound image. Such errors can be detrimental in medical procedures, such as needle biopsy procedures planned with ultrasound images. It is noted that if the ultrasound imaging is being conducted while the needle is in the pass zone Z1, the position of the needle and the site of interest will typically be shifted proportionally and location of the site of interest will not be compromised. If a surgeon is relying on images where the needle is not in the pass zone, however, such geometric errors could prevent the precise biopsy guidance.

In this embodiment, the controller 14 corrects the displacement of the focal point P12 due to refraction by the tissue region 80 in step 56 by generating forward or reverse ray segments between the desired focal point P12 and each transducer element. The rays are drawn taking into consideration Snell's law (Equation 3), the segmented boundaries and the speeds of sound in the tissue region 80 and adjacent tissue regions, as described above with respect to FIG. 6. Since the rate of change of the depth of the tissue region 80 is monotonic and linear, traversal of the tissue region 80 by the ultrasound beams affects all the beams proportionally. The phases of the beams are shifted in such a way that the ultrasound beams are steered. Constructive interference at the shifted focal point P14 is not, therefore, appreciably degraded.

In providing the aberration correction due to compensation for the shift in the focal point to bring the shifted focal point P16 back to the focal P12 selected by a user, the propagation times of each refracted beam is determined by the ray calculation, as discussed above. For example, an ultrasound beam emitted by the transducer element 33$a$ along a ray segment R22 element will be refracted by the tissue region 80 to form beams along rays R24 and R26. The beam corresponding to the ray R26 will intercept the focal point R12. The propagation times of ultrasound beams corresponding to the rays R22, R24, R26 are used to determine the transmission delay for the transducer element 33$a$. Rays are similarly computed for the other transducer elements of the array 32 to provide beams focused on the focal point P12.

While the correction for focal point shift is inherent in the correction process when refraction is considered, as described herein, the software implementing the correction process may allow for separation corrections for defocusing (decrease in constructive interference) and focal point shift. There may be circumstances where it may only be necessary or may only be beneficial to correct for one or the other. For example, when ultrasound images are used for visual diagnosis, small geometric shifts in objects in the image may not interfere with the evaluation of the image. It may not, therefore, be necessary to correct for focal point shift. If the ultrasound image is to be used to guide a needle biopsy procedure, in contrast, even small geometrical shifts in objects in the image may be critical and need to be corrected, as discussed above.

Figure 8:
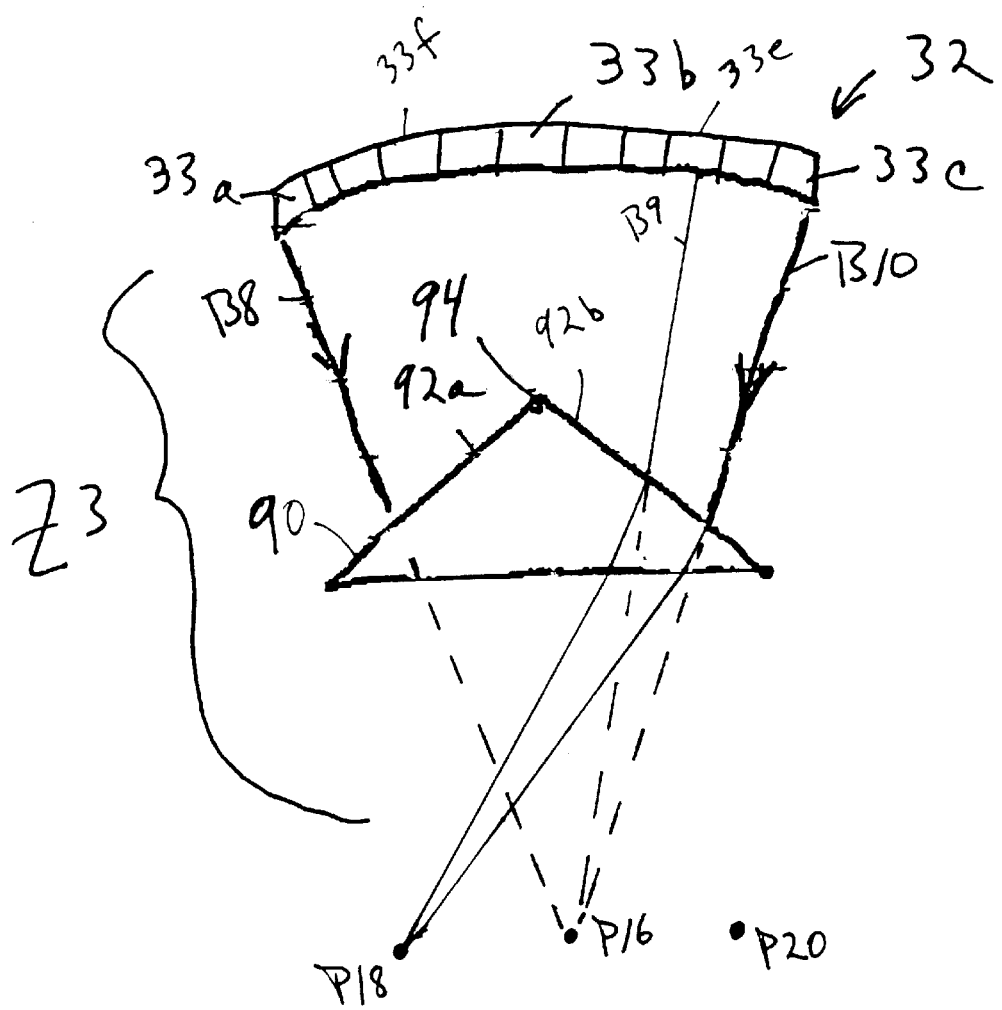
FIG. 8 is a schematic representation of refraction of ultrasound beams caused by another a prism shaped tissue region with a vertex facing the ultrasound beams.

FIG. 8 is an example of another segmented tissue region 90 that may be modeled as a prism, where two faces 92a, 92b and a vertex 94 of the prism intercept the ultrasound beams transmitted by the transducer array 32. In FIG. 8, the tissue region 90 is positioned such that the ultrasound beams transmitted by the transducer array 32 are substantially bisected. Here, three exemplary ultrasound beams B8, B9, B10 are shown being transmitted by the three respective transducer elements 33a, 33e, 33c. The ultrasound beams B8, B9, B10 are intended to be focused onto a focal point P16. However, due to refraction by the prism shaped tissue region 90, which bisects the ultrasound beams transmitted by the transducer array 32, the ultrasound beams B9 and B10, and other ultrasound beams transmitted by the transducer elements 33 that impinge on the face 92b, are focused onto a focal point P18. The ultrasound beam B8, and other ultrasound beams transmitted by the transducer elements 33 that impinge on the face 92a, will be focused on a focal P20. The ultrasound beams focused on the focal point P20 are not shown to simplify the illustration. The focal points, P18 and P20 are symmetrically positioned with respect to the original focal point P16. Each shifted focal point P18, P20 receives about half of the ultrasound energy that would be received at the original focal point P16.

Segmentation of the ultrasound image or images and computation of the transmission delay times may be conducted in nearly real-time. In one embodiment, as a user holds the ultrasound probe 12 of FIG. 1 in place, the user can switch on a tissue aberration correction mode to implement the method 50, or other such method in accordance with the invention. The system 10 will automatically conduct the initial scan of step 52, automatically segment the image in step 54 and compute adjusted delay times in step 56, in one or a few seconds, and then conduct a corrected imaging scan employing the adjusted delay times in step 58. The process may be conducted so quickly that the ultrasound probe 12 will be in the same position, within tolerances, with respect to the patient and focal point P during the initial and corrected imaging scars. If the operator feels that the position of the ultrasound probe 12 has moved beyond the acceptable tolerances, the operator can initiate a new initial scan and subsequent steps of the process.

A motion tracker, such as an electromagnetic motion tracker, may also be used to correlate the position of the ultrasound probe 12 during the initial ultrasound imaging scan of step 52 to a subsequent position of the ultrasound probe during the corrected ultrasound imaging scan in step 58, if necessary. The adjusted propagation times may thereby be further adjusted based on the new position of the ultrasound probe 12. A "Flock of Birds®" electromagnetic tracker, available from Ascension Technology Corporation, Burlington, Vermont, may be used, for example.

Alternatively, the user may decide whether to implement the tissue correction mode based on the quality of an image or images from the initial ultrasound imaging scan. The motion tracker discussed above, or other such motion tracker, may be used to correlate the position of the ultrasound probe 12 during the initial ultrasound imaging scan and the corrected ultrasound imaging scan.

Instead of computing new propagation times from each transducer element 33 to the focal point P and other points in the pass zone to compute new transmission and reception delays, as described above, the delay times computed in step 56 may be based on phase shifts caused by traversal through tissue regions where the actual speed of sound in that region is not the same as the average speed of sound. The phase shift may be used by the controller 14 to determine adjustments to the original time delays for each transducer element so that the ultrasound beams constructively interfere at the focal points P.

The phase shift φ, in degrees, introduced to an ultrasound beam due to traversal through a tissue region where the speed of sound is different than the average speed of sound in tissue is:

$$\phi = 360 f D \, (1/C_A - 1/C_T), \tag{4}$$

where F is the driving frequency, $C_A$ is the average speed of sound in tissue (1540 m/s), $C_T$ is the actual speed of sound in the tissue and D is the distance traveled in the tissue. Once the phase shifts caused by the one or more segmented tissue regions is determined, the original delay times may be adjusted by the controller 14 to compensate.

The imaging parameters for the initial images derived in step 52 may be different from the imaging parameters used in step 58, to optimize for segmentation or imaging, respectively. For example, low frequency sound waves penetrate tissue more deeply than higher frequency sound waves and are less susceptible to tissue aberrations. Images resulting from the use of low frequencies, however, have less contrast resolution than images resulting from the use of higher frequencies. Low frequencies may therefore provide better images for segmentation and may therefore be used in conducting the initial, conventional imaging scan of step 52. Higher frequencies may then be used in the corrected ultrasound imaging of step 58 to obtain higher images with better contrast resolution.

In one example, the ultrasound transducer elements 33 of the transducer array 32 may be wide bandwidth transducer elements having a range of 1.5–4.0 Megahertz ("MHz"). The initial ultrasound scan in step 52 may be conducted at a frequency of 1.5 MHz and the corrected ultrasound imaging scan of step 58 may be conducted at a frequency of 4.0 MHz. The frequency range may vary dependent upon the clinical application.

Figure 9:
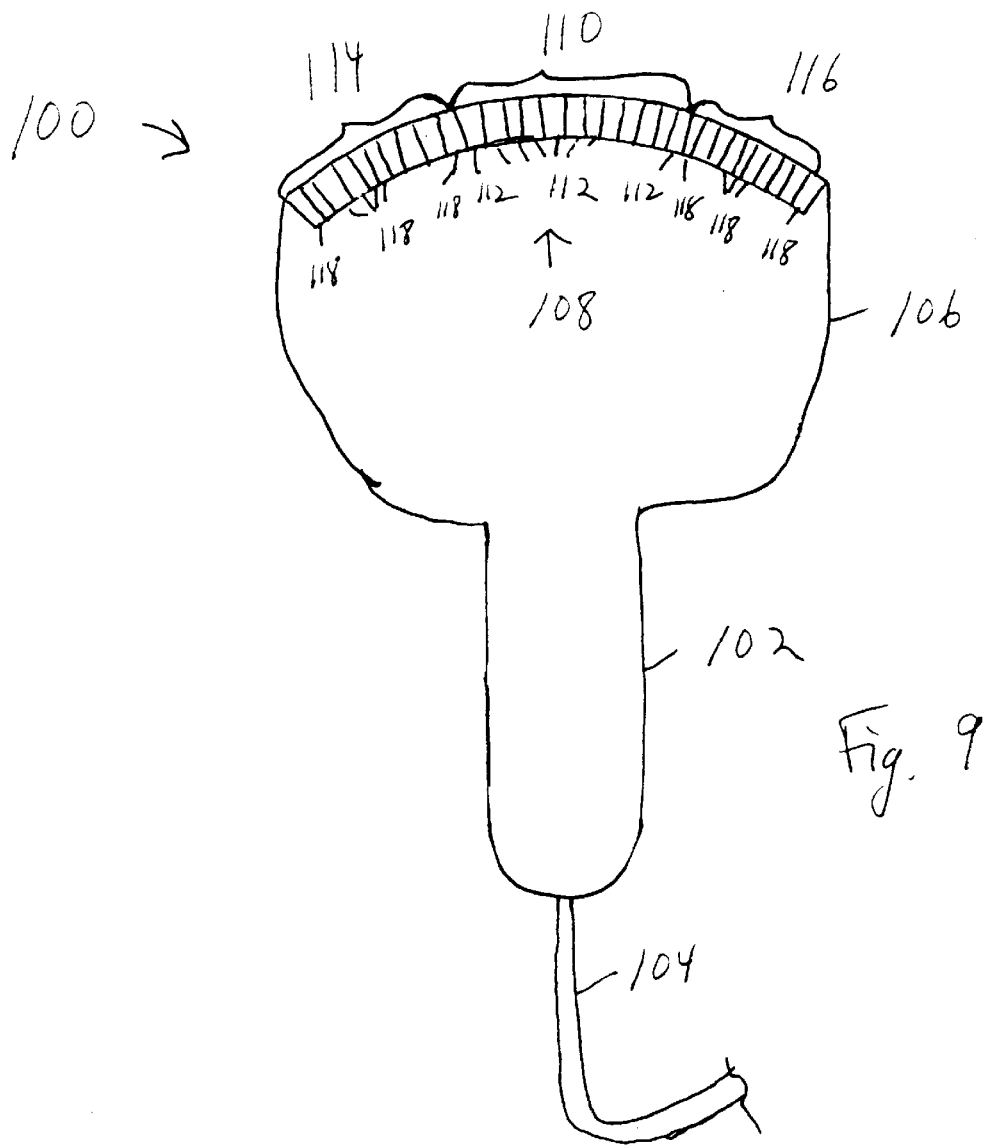
FIG. 9 is a schematic representation of an ultrasound probe comprising high and low frequency transducer elements.

Alternatively, the ultrasound probe 12 may comprise multiple sections of transducer elements, each for transmitting ultrasound beams at a high or low frequency. For example, FIG. 9 is a schematic representation of a side view of an ultrasound probe 100 in accordance with another embodiment comprising a handle 102, a cable 104 and a body portion 106 supporting a transducer array 108. The transducer array 108 is a linear curved array comprising a central section 110 of low frequency transducer elements 112 and outer sections 114, 116 comprising high frequency transducer elements 118.

The transducer elements 112 of the central section 110 may be driven by the beam former 18 at a low frequency, such as 1.0 MHz, for example, during the initial ultrasound imaging scan of step 52. The transducer elements 118 of the high frequency sections 114, 116 may then be driven by the beam former 18 at a high frequency, such as 4.0 MHz, during ultrasound imaging with the adjusted delay times in step 58. It is preferred to locate the outer, high frequency sections 114, 116 at respective sides of the low frequency central section 110 so that the high frequency ultrasound beams transmitted during the corrected ultrasound imaging scan of step 58 have a maximum aperture. In a matrix transducer array, the high frequency transducers 118 are preferably provided around the periphery of the matrix, while the low frequency transducers 112 are preferably provided in a central portion of the matrix.

Other configurations may be used, as well. Separate low and high frequency ultrasound probes 12 may also be used for the initial and subsequent imaging scans, in conjunction with tracking, as discussed above.

Figure 10:
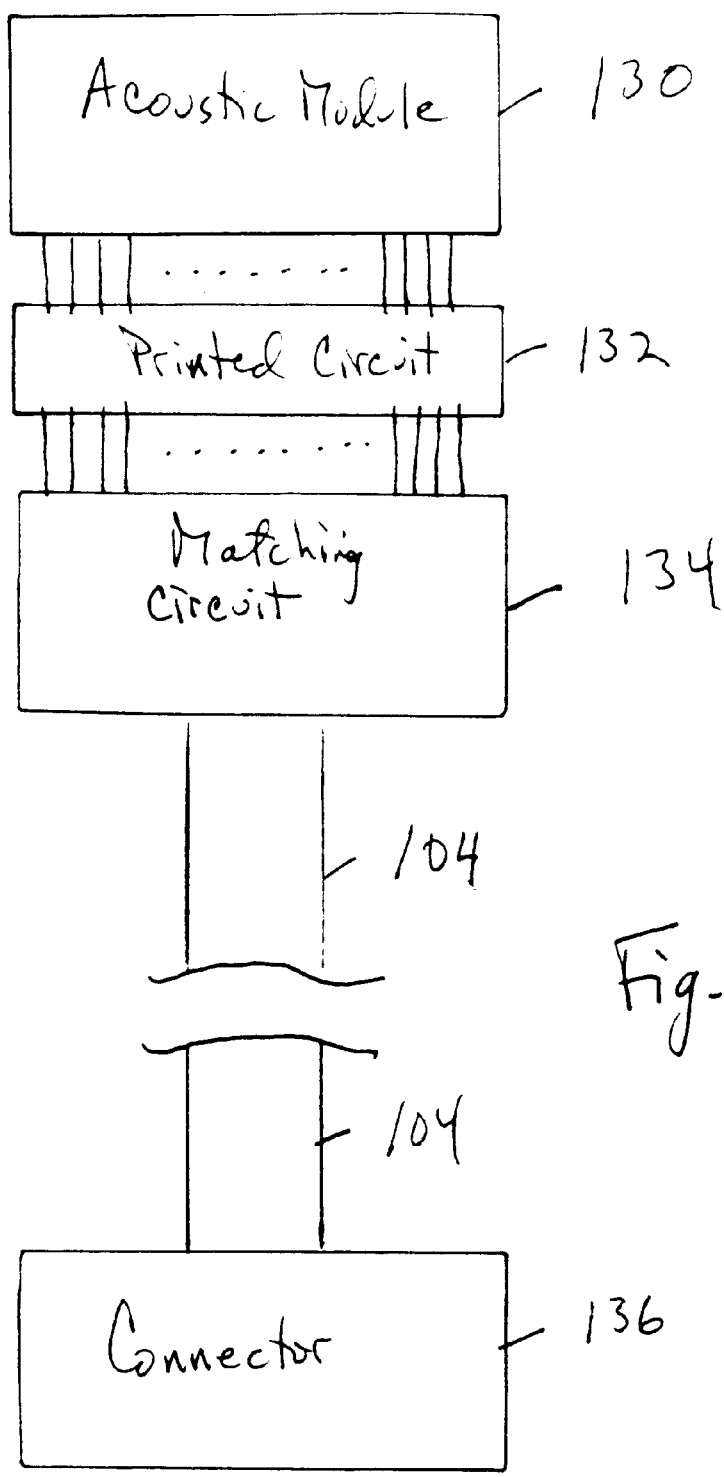
FIG. 10 is a block diagram of elements of the ultrasound probe of FIG. 9.

FIG. 10 is a block schematic diagram of the electronic components of the ultrasound probe 100 of FIG. 9. An acoustic module 130 includes the high and low frequency transducer elements 112, 118 (not shown in this view). Electrical connectors, such as wires, connect each transducer element 112, 118 to connectors of a printed circuit 132, which electrically couples the acoustic module 130 to the cable 104. A matching circuit 134 is optionally provided to match the impedance between the transducer elements 112, 118 and the front end electronics. The cable 104 is connected to a multi-pin connector 136 for electrical coupling to the beam former 18.

Other imaging parameters that may be varied include the pulse shape of an individual ultrasound pulse and the burst length of ultrasound pulses or cycles. A wider pulse, which has a higher energy content and lower frequency content, may provide better images for segmentation in the initial ultrasound imaging scan of step 52. A shorter pulse, which has a higher frequency content, may provide better contrast resolution in the corrected ultrasound imaging of step 58. A longer burst length may also provide a better image for segmentation while a shorter burst length, in conjunction with a higher frequency, may provide better contrast resolution in step 58. Pulse shape and burst length may also be varied by the beam former 18, under the control of controller 14.

As mentioned above, there is some variability in the reported speeds of sound in different body tissues. We have found that the speeds of sound used herein provide good correction for tissue aberration due to tissue inhomogeneity.

While preferred embodiments and certain alternatives have been described above, it is to be understood that various changes may be made to those embodiments without departing from the spirit or scope of the invention, which is defined in the claims, below.

What is claimed is:

1. A method of imaging a site of interest in a body using an ultrasound probe, the ultrasound probe comprising a plurality of ultrasound transducer elements, the method comprising:

obtaining an ultrasound image of a pass zone of the body between the site of interest and the ultrasound probe, the image including the site of interest and a plurality of tissue regions in the pass zone;

determining, from the image, boundaries of a selected tissue region in the pass zone;

computing respective focusing delay times for each transducer element associated with an ultrasound beam passing through the selected tissue region, the computed focusing delay times computed based, at least in part, on a speed of sound in, and the determined boundaries of, the selected tissue region, wherein the speed of sound is a speed other than an average speed of sound in body tissue; and conducting an ultrasound imaging scan of the pass zone employing the computed focusing delay times.

2. The method of claim 1, wherein the computed focusing delay times are computed transmission delays, the method comprising:

computing a respective computed transmission delay for each transducer element transmitting an ultrasound beam through the selected tissue region, each computed transmission delay computed such that ultrasound beams transmitted by respective transducer elements will constructivly interfere at a selected focal point.

3. The method of claim 2, comprising computing the respective computed transmission delays, at least in part, by conducting a ray calculation between the focal point and each transducer element transmitting an ultrasound beam through the selected tissue region, to determine a respective distance traveled by each ultrasound beam through the selected tissue region, based on the determined boundaries.

4. The method of claim 3, further comprising:

determining a respective initial transmission delay for each transducer element of the plurality based, at least in part, on an average speed of sound in body tissue for each one of the plurality of tissue regions in the pass zone; and conducting an initial ultrasound imaging scan of the site of interest employing the initial transmission delays to obtain ultrasound image of the site of interest;

wherein computing the respective computed transmission delays comprises determining a respective adjustment to the initial transmission delay for each transducer element transmitting an ultrasound beam through the selected tissue region, the adjustments based, at least in part, on a phase shift for each ultrasound beam, the phase shift due to passage through the selected tissue region.

5. The method of claim 3, wherein conducting the ray calculation comprises determining refraction of ultrasound beams passing through the selected tissue region at a boundary of the selected tissue region.

6. The method of claim 1, wherein the computed focusing delay times are computed reception delays, the method comprising:

computing respective computed reception delays for each transducer element receiving an ultrasound beam passing through the selected tissue region, the respective computed reception delays computed such that ultrasound beams reflected from reflecting bodies in the pass zone are in phase after detection.

7. The method of claim 6, comprising computing the computed reception delays, at least in part, by conducting a ray calculation between a reflecting body in the pass zone and each transducer element receiving a respective ultrasound beam traveling through the selected tissue region from the reflecting body, to determine a respective distance traveled by the ultrasound beam between the reflecting body and each transducer element.

8. The method of claim 7, comprising:

computing respective initial reception delays for each transducer element of the plurality based, at least in part, on an average speed of sound in body tissue for each one of the plurality of tissue regions in the pass zone; and conducting an initial ultrasound imaging scan of the site of interest employing the initial transmission delays to obtain the ultrasound image of the site of interest;

wherein computing the respective computed reception delays comprises determining a respective adjustment to the initial reception delays for each transducer element receiving an ultrasound beam passing through the selected tissue region, the adjustments based, at least in part, on a phase shift for each ultrasound beam, the phase shift due to passage through the selected tissue region.

9. The method of claim 7, wherein conducting the ray calculation comprises determining refraction of ultrasound beams passing through the selected tissue region at a boundary of the selected tissue region.

10. The method of claim 1, wherein computing the respective computed focusing delay times comprises:
   determining a respective propagation time between each transducer element and respective points in the pass zone based, at least in part, on a speed of sound that is about the speed of sound in the selected tissue region and a respective distance traveled by an ultrasound beam through the selected tissue region, based on the determined boundaries.

11. The method of claim 1, further comprising computing the respective computed focusing delay times based, at least in part, on refraction of each ultrasound beam passing through the selected tissue region at the boundaries of the selected tissue region.

12. The method of claim 11, comprising computing the respective computed focusing delay times to only correct for displacement of a focal point.

13. The method of claim 11, comprising computing the respective computed focusing delay times to only correct for defocusing at a focal point.

14. The method of claim 1, further comprising:
   computing respective initial delay times for each transducer element of the plurality based, at least in part, on an average speed of sound in body tissue for each one of the plurality of tissue regions in the pass zone; and
   obtaining the ultrasound image of the pass zone by conducting an initial ultrasound imaging scan of the site of interest employing the initial focusing delay times.

15. The method of claim 1, wherein the selected tissue region is a region of fat tissue.

16. The method of claim 15, further comprising computing the respective computed focusing delay times based, at least in part, on a uniform speed of sound through non-selected soft tissue regions.

17. The method of claim 16, wherein the uniform speed of sound is about a speed of sound in muscle tissue.

18. The method of claim 17, further comprising:
   determining, from the image, boundaries of an additional selected tissue region in the pass zone;
   wherein the respective focusing delay times are computed based, at least in part, on a speed of about a speed of sound in the additional selected tissue region and on the determined boundaries of the additional selected tissue region.

19. The method of claim 1, wherein the selected tissue region is from the group consisting of fat tissue, muscle tissue, organ tissue. and bone tissue.

20. The method of claim 1, wherein the boundaries of the selected tissue region are determined from the image by segmenting the selected tissue region from adjacent tissue regions.

21. The method of claim 1, comprising:
   obtaining a plurality of ultrasound images of the pass zone, each image comprising a different sectional plane through the site of interest;
   determining, from each image, the boundaries of the selected tissue region; and
   determining a three dimensional boundary of the selected tissue region, based on the determined boundaries from each image.

22. The method of claim 1, wherein the ultrasound image is obtained by conducting an initial ultrasound imaging scan, wherein at least one imaging parameter used in the first ultrasound imaging scan is different than an imaging parameter used in the ultrasound imaging scan employing the computed focusing delay times.

23. The method of claim 22, wherein the imaging parameter is from a group consisting of transmission frequency, transmission pulse shape and transmission burst length.

24. The method of claim 1, wherein:
   the ultrasound image is obtained by conducting a three dimensional ultrasound imaging scan; and
   the determined boundaries of the selected tissue region are three dimensional.

25. The method of claim 1, further comprising:
   obtaining a second ultrasound image of the pass zone based on the ultrasound imaging scan;
   determining, from the second ultrasound image, second boundaries of the selected tissue region;
   computing second respective focusing delay times for each transducer element associated with an ultrasound beam passing through the selected tissue region, the second focusing delay times computed based, at least in part, on the speed of sound in, and the determined second boundaries of, the selected tissue region; and
   conducting a second ultrasound imaging scan of the pass zone, employing the second computed focusing delay times.

26. The method of claim 1, wherein the speed of sound other than the average speed of sound is a speed of sound in the tissue type of the selected tissue region.

27. A method of imaging a site of interest in a body using an ultrasound probe, the ultrasound probe comprising a plurality of ultrasound transducer elements, the method comprising:
   conducting a first ultrasound imaging scan of a pass zone of the body between the site of interest and the ultrasound probe with the ultrasound probe, wherein the pass zone comprises a plurality of tissue regions and the first ultrasound imaging scan employs initial transmission delays and initial reception delays for each transducer element, the initial transmission and reception delays being based, at least in part, on an average speed of sound in body tissue for each one of the tissue regions in the pass zone;
   obtaining an ultrasound image of the pass zone from the first ultrasound imaging scan, the image including the site of interest and the plurality of tissue regions in the pass zone;
   segmenting a selected tissue region from surrounding tissue regions in the image;
   computing a respective adjusted transmission delay for each transducer element transmitting an ultrasound beam through the selected tissue region, each adjusted transmission delay computed based, at least in part, on a speed about a speed of sound in, and the segmented boundaries of, the selected tissue region, such that ultrasound beams transmitted by the plurality of transducer elements will constructively interfere at a selected focal point proximate the site of interest;
   computing respective adjusted reception delays for each transducer element receiving an ultrasound beam passing though the selected tissue region, the adjusted reception delays being computed based, at least in part, on a speed about a speed of sound in, and the segmented boundaries of, the selected tissue region, such that ultrasound beams reflected from reflecting bodies in the pass zone are in phase after detection; and conducting a second ultrasound imaging scan of the site of interest employing the adjusted transmission delays and the adjusted reception delays.

28. The method of claim 27, wherein the selected tissue region is at least one of a fat tissue region and a bone tissue region.

29. The method of claim 28, further comprising computing the respective focusing delay times based, at least in part, on refraction of ultrasound beams passing through the selected tissue region at the boundaries of the selected tissue region.

30. The method of claim 28, further comprising:
obtaining a second ultrasound image of the pass zone based on the second ultrasound imaging scan;
determining, from the second ultrasound image, second boundaries of the selected tissue region;
computing a second respective focusing delay time for each transducer element associated with an ultrasound beam passing through the selected tissue region, the second focusing delay times computed based, at least in part, on the speed of sound in, and the determined second boundaries of, the selected tissue region; and
conducting a second ultrasound imaging scan of the pass zone, employing the second focusing delay times.

31. The method of claim 27, wherein:
the selected tissue region is a fat tissue region; and
the plurality of tissue regions comprises other soft tissue regions including a muscle tissue region;
the method further comprising:
computing the respective adjusted transmission delays and the respective adjusted reception delays based, at least in part, on a speed about an actual speed of sound in muscle tissue for the other soft tissue regions.

32. The method of claim 27, wherein the speed of sound in the selected tissue region is about a speed of sound in the selected tissue region.

33. An ultrasound imaging system comprising:
an ultrasound imaging probe comprising a plurality of transducer elements; wherein the system is configured to:
determine, from ultrasound imaging data obtained of a pass zone between a site of interest in a body and the ultrasound probe, boundaries of a selected one of a plurality of tissue regions in the pass zone; and
compute a respective focusing delay time for each transducer element associated with an ultrasound beam passing through the selected tissue region during imaging, the delay times computed based, at least in part, on a speed of sound in, and the determined boundaries of, the selected tissue regions, wherein the speed of sound is other than an average speed of sound in body tissue.

34. The system of claim 33, further comprising:
a beam former coupled to the ultrasound probe to provide driving signals to the transducer elements and to receive ultrasound signals detected by the transducer elements;
at least one processor coupled to the beam former to receive detected ultrasound signals and process the received signals for display; and
a controller coupled to the beam former to compute the respective focusing delay times and to provide the delay times to the beam former.

35. The system of claim 33, wherein the respective focusing delay times are transmission delays, the system configured to compute:
a respective transmission delay for each transducer element transmitting an ultrasound beam through the selected tissue region, each transmission delay computed such that ultrasound beams transmitted by respective transducer elements will constructively interfere at a selected focal point.

36. The system of claim 33, wherein the respective focusing delay times are reception delays, the system configured to:
compute respective reception delays for each transducer element receiving an ultrasound signal passing through the selected tissue region, the respective reception delays being computed such that ultrasound beams reflected from reflecting bodies in the pass zone are in phase after detection.

37. The system of claim 33, configured to determine the boundaries of the selected tissue region by segmenting the selected tissue region from adjacent tissue regions.

38. The system of claim 33, further configured to:
obtain ultrasound imaging data of a plurality of sectional planes through the site of interest;
determine, from the imaging data, the boundaries of the selected tissue region, and
determine a three dimensional boundary of the selected tissue region based on the determined boundaries from each image.

39. The system of claim 33, configured to determine, from three dimensional ultrasound imaging data, a three dimensional boundary of the selected tissue region in the pass zone.

40. The system of claim 33, further comprising computing the respective focusing delay times based, at least in part, on refraction of ultrasound beams passing through the selected tissue regions at the boundaries of the selected tissue region.

41. The system of claim 33, wherein the ultrasound probe comprises low frequency transducer elements and high frequency transducer elements.

42. The system of claim 33, wherein the speed of sound other than the average speed of sound is about a speed of sound in the selected tissue region.

43. The system of claim 42, wherein the speed of sound other than the average speed of sound is the speed of sound in the selected tissue region.

44. The system of claim 33, wherein the selected tissue region is from the group consisting of fat tissue, muscle tissue and bone tissue.

45. Software residing on a machine readable medium for operating a system for imaging of a site of interest in a body using an ultrasound probe, the ultrasound probe comprising a plurality of transducer elements, the software comprising instructions for causing the system to:
determine, from ultrasound imaging data obtained of a pass zone between a site of interest in the body and the ultrasound probe, boundaries of a selected one of a plurality of tissue regions in the pass zone; and
compute a respective focusing delay time for each transducer element associated with an ultrasound beam passing through the selected tissue region during imaging, the focusing delay times computed based, at least in part, on a speed of sound in, and the determined boundaries of, the selected tissue region, wherein the speed of sound is other than an average speed of sound in body tissue.

46. The software of claim 45, wherein the focusing delay times are transmission delays, the software comprising instructions for causing the system to:
compute a respective transmission delay for each transducer element transmitting an ultrasound beam through the selected tissue region, each transmission delay being computed such that ultrasound beams transmitted by respective transducer elements will constructively interfere at a selected focal point.

47. The software of claim 45, wherein the focusing delay times are reception delays, the computer program comprising instructions for causing the system to:
compute respective reception delays for transducer elements receiving ultrasound beams passing through the selected tissue region, the reception delays being computed such that ultrasound beams reflected from reflecting bodies in the pass zone will be in phase.

48. The software of claim 45, further comprising instructions to:
provide the respective computed focusing delay times to a beam former; and
conduct ultrasound imaging of the site of interest employing the computed adjusted delay times.

49. The software of claim 45, comprising instructions to determine the boundaries of the region by segmenting the tissue region from adjacent tissue regions.

50. The software of claim 45, comprising instructions to:
determine the boundaries of the selected tissue region from ultrasound imaging data of a plurality of sectional planes through the site of interest; and
determine a three dimensional boundary of the selected tissue region based on the determined boundaries.

51. The software of claim 45, comprising instructions to determine, from three dimensional ultrasound imaging data, a three dimensional boundary of the selected tissue region in the pass zone.

52. The software of claim 45, further comprising computing the respective focusing delay times based, at least in part, on refraction of ultrasound beams passing through the selected tissue region at the boundaries of the selected tissue region.

53. The software of claim 45, wherein the speed of sound other than the average speed of sound is about a speed of sound in the selected tissue region.

54. The software of claim 45, wherein the selected tissue region is from the group consisting of fat tissue, bone tissue and muscle tissue.

55. A method of computing focusing delay times for use in ultrasound imaging of a site of interest in a body using an ultrasound probe, the ultrasound probe comprising a plurality of ultrasound transducer elements, the method comprising:
determining, from ultrasound imaging data of a pass zone between a site of interest in the body and the ultrasound probe, boundaries of a selected one of a plurality of tissue regions in the pass zone; and
computing respective focusing delay times for each transducer element associated with an ultrasound beam passing through the selected tissue region during imaging, the respective delay times being computed based, at least in part, on a speed of sound in, and the determined boundaries of, the selected tissue region, wherein the speed of sound is other than an average speed of sound in body tissue.

56. The method of claim 55, wherein the focusing delays are transmission delays, the method comprising:
computing a respective transmission delay for each transducer element transmitting an ultrasound beam through the selected tissue region, the transmission delays computed such that ultrasound beams transmitted by respective transducer elements will constructively interfere at a focal point proximate the site of interest, wherein the speed of sound other than the average speed of sound is about a speed of sound in the selected tissue region; and
computing respective reception delays for each transducer element receiving an ultrasound beam passing through the selected tissue region, the reception delays computed such that ultrasound beams reflected from reflecting bodies in the pass zone are in phase, wherein the speed of sound other than the average speed of sound is about a speed of sound in the selected tissue region.

57. The method of claim 55, further comprising computing the respective focusing delay times based, at least in part, on refraction of ultrasound beams passing through the selected tissue regions at the boundaries of the selected tissue region.

* * * * *